March 21, 1961 R. WELLINGTON Plant Pat. 2,035
CRAB APPLE TREE
Filed June 8, 1960
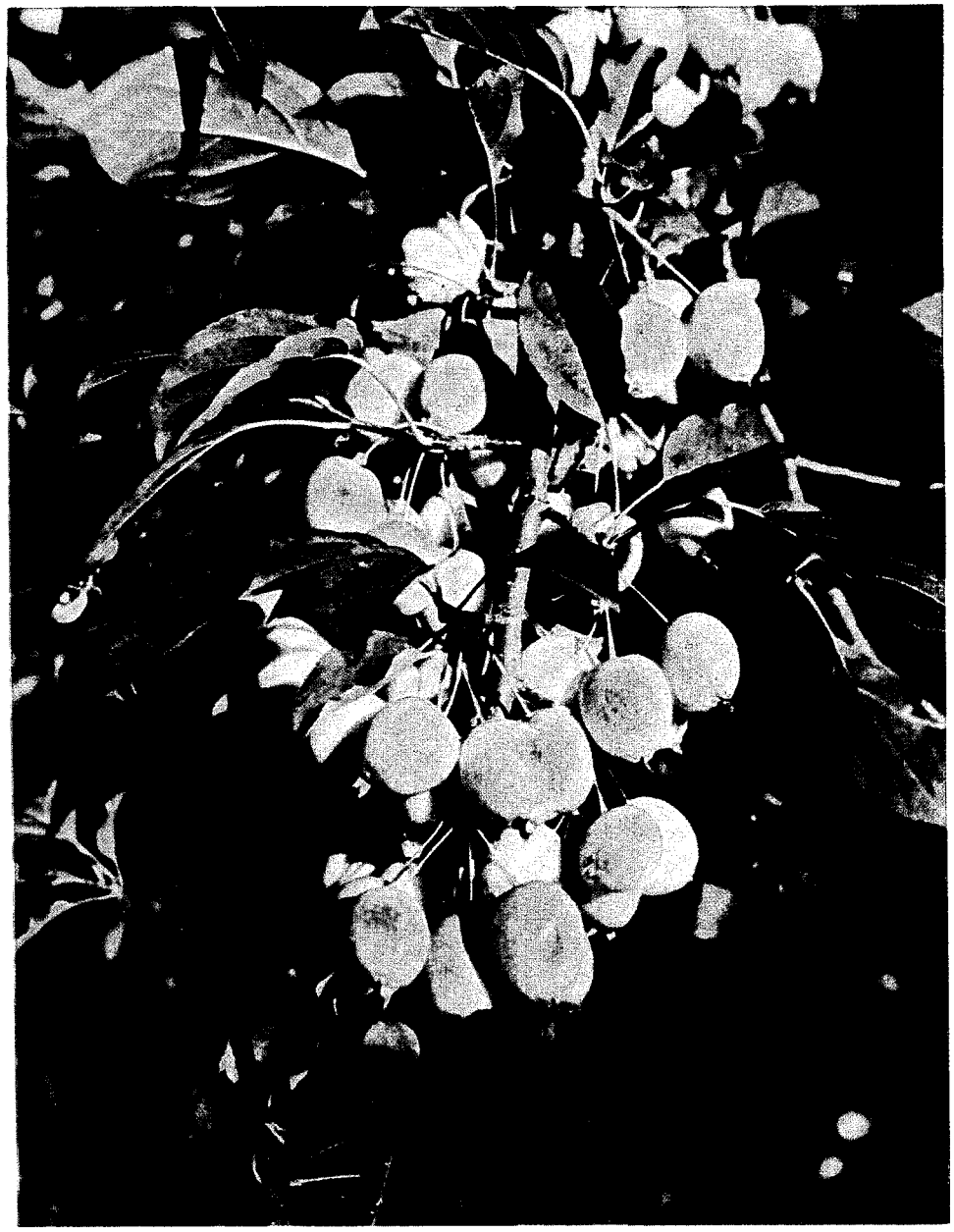
INVENTOR
Richard Wellington
BY Robb & Robb
ATTORNEYS United States Patent Office Plant Pat. 2,035
Patented Mar. 21, 1961

2,035

CRAB APPLE TREE

Richard Wellington, Geneva, N.Y., assignor to Stark Bro's Nurseries & Orchards Company, Louisiana, Mo., a corporation of Missouri Filed June 8, 1960, Ser. No. 34,855

1 Claim. (Cl. 47—62)

The present invention relates to a new and distinct variety of crab apple tree which was discovered by me as a newly found seedling on my cultivated property at Geneva, New York.

At the time of my discovery aforesaid, I was growing various fruit trees on my property, amongst which was a Bing cherry tree. I discovered the new crab apple tree as a small seedling which came up under this cherry tree and out of curiosity, I left the young seedling to continue its growth and come into fruiting. By carefully preserving the seedling and continuing close observations thereof, I found that it came into bearing early and bore fruit annually. The fruit was found to be both attractive and capable of making excellent jelly. Although it was not sprayed for a number of years, the new seedling showed little or no evidence of scab, no fire blight, and complete absence of any injury attributed to insects, such as the codling moth.

The new seedling proved to be a vigorous and rapid grower and it was therefore headed back from time to time to prevent it from overcrowding or interfering with the overhead branches of the Bing cherry tree. This pruning dwarfed the original tree and upset its natural symmetry. However, it continued to produce attractive flower buds and open blossoms, and these flowers, together with the red colored fruit made the new seedling crab apple a very attractive ornamental. Unlike most crab apple trees, the fruit did not drop when mature but remained on the tree and provided food for birds through the winter and spring seasons following each new crop. From 2 to 7 fruit were borne on the spurs and occasionally on the terminals, yet the extremely heavy cropping did not hamper the production in succeeding years.

Although the parentage of my new crab apple seedling is not definitely known, it is believed to be a seedling of the species *Malus arnoldiana,* since the new seedling has certain tree, blossom and fruit characteristics that are similar to those of that species, while other characteristics such as size, pubescence on the twigs, leaves and fruit more nearly correspond to those of *Malus pumila* Mill. An *arnoldiana* crab apple tree was located near the point where by new seedling was discovered, and it is quite possible that a seed of that nearby *arnoldiana* tree was dropped by a bird while perched on the overhanging branch of the Bing cherry tree under which the new seedling sprang up.

Briefly summarizing the outstanding characteristics of my new crab apple seedling, the following are particularly noted as representing a unique combination of features which differentiate the new seedling from all other varieties of which I am aware:

(1) Attractive pendulous flowers and high coloring of the fruit, which combine to make a very desirable ornamental tree;

(2) An early bearing habit (has fruited in the second year, while other varieties such as "Dolgo" [unpatented] generally do not bear until at least the 5th year);

(3) A heavy and regular bearing habit (more so than the variety "Dolgo," with spurs producing from 3 to 7 fruit, while 5 is the average number);

(4) A relatively late ripening habit and longer retention of the fruit on the tree than is the case of the variety "Dolgo" (ripening about one month later than "Dolgo");

(5) Suitability of the fruit to make excellent jelly; and (6) Good resistance to scab, fire blight and insect injury such as that attributed to codling moth, even without spraying, and no injury attributed to spraying with commonly used spray materials, when utilized, whereas the flesh of the fruit of "Dolgo" tends to break down as soon as the fruit becomes ripe in those instances where the trees have been sprayed.

Asexual reproduction of my new crab apple variety by budding, as performed by me at Geneva, New York, shows that the foregoing characteristics and distinctions come true to form and are established and transmitted through succeeding propagations.

The accompanying drawing shows typical specimens of the fruit and foliage of my new variety as depicted in color as nearly true as it is reasonably possible to make the same in a color illustration of this character.

The following is a detailed description of my new variety, with color terminology in accordance with Ridgway's Color Standards and Nomenclature (hereinafter abbreviated as "Ridgway"), also the Horticultural Color Guide (hereinafter abbreviated as "HCG"), and Munsell Color Chart (hereinafter abbreviated as "Munsell"), as indicated, except where general color terms of ordinary dictionary significance are obvious:

(Observations made from specimens grown at Geneva, New York.)

Dates first and last pickings: About September 20 and about October 15, respectively; fruit will hang all winter.

Tree: Large; vigorous; upright, but drooping after fruiting; tall; round-topped; rapid growing; hardy; very productive; regular bearer.

*Trunk.*—Stocky; shaggy at base of oldest wood.

*Branches.* — Medium thickness; smooth; much-branched.

*Twigs.*—Color—Prouts Brown, Plate XV, Color No. 15′, tone M (Ridgway).

*Lenticels.*—Numerous; medium size on branchlets, but large on old wood.

*Leaves.*—Medium size (about 3½ inches long, and about 2 inches wide); ovate; taper-pointed; medium thickness; nearly smooth. Margin—finely serrate. Color—Varley's Green, Plate XVIII, Color No. 31′, tone M (Ridgway). Petiole—medium length (about 1¼ inches); slender.

Flowers: Medium late in comparison with other varieties; medium size.

*Date of first bloom.*—About May 4.

*Date of full bloom.*—About May 9.

*Color.*—Moderate Purplish Pink, Plate 2.5 R.P. 8/5 (Munsell), changing to white.

Fruit:

*Maturity when described.*—Eating ripe (about September 20, and holds good condition from 3 to 4 weeks).

*Size.* — Uniform. Axial diameter — 1 9/16 inches. Transverse diameter—1½ inches.

*Form.*—Truncate at base; oblong-ovoid; conical; slightly ribbed.

*Cavity.*—Nearly symmetrical; lipped slightly toward apex. Depth—⅛ inch. Breadth—½ inch.

*Basin.*—Crowned; memmiform; about 5/16 inch broad. Markings—5 roundish protuberances and faintly ridged.

*Stem.*—Clubbed; slender; pubescent. Length—1½ inches. Breadth—1/20 inch. Markings—often with 1 or 2 small protuberances.

*Calyx.*—Closed; segments persistent; narrowly lanceolate; acuminate; about ¼ inch long; separated; erect; reflexed at apex; connivent; both inner and outer surfaces pubescent.

*Eye.*—Medium size; closed.

*Skin.*—Thin; medium toughness; smooth; glossy; waxed. Dots—obscure; many; small; even; submerged; color—whitish; distribution—fairly even. Ground color—light yellow. Color markings—very slightly mottled; bright; color—mostly solid Chrysanthemum Crimson, Plate 824/1, page 169, vol. 2 (HCG).

*Bloom.*—Scant.

*Scarfskin.*—White.

*General color effect.*—Attractive red.

*Flesh.* — Juicy. Color — white. Texture — firm. Flavor—sprightly (1.89% citric acid equivalent). Aroma—distinct. Quality—good.

*Core.*—Median. Bundle area—medium; broadly ovate. Halves of core—equal. Bundles—inconspicuous; color—yellowish. Core lines—clasping. Carpellary area—distinct. Calyx tube—pubescent; cone-shaped; funnel stem of medium length; entire depth ¼ inch. Styles—united toward base; pubescent. Stamens—marginal.

*Axiallary cavity.*—Wanting.

*Seed cells.*—From axile to abaxile; from closed to partly open. Cell walls—thin. Length—7/16 inch. Breadth—3/16 inch.

*Longitudinal section.*—Narrowly oval; emarginate; surface entire; narrow cross section.

Seeds:

*Number.*—Average 6 perfect, and from 1 to 3 imperfect; largest number per cell from 8 to 10.

*Length.*—5/16 inch.

*Breadth.*—5/32 inch.

*Form.*—Acute.

*Color.*—Brown (light brown when dry).

Use: Local; culinary (excellent for jelly).

Keeping quality: Medium; about 30 days in ordinary storage.

Insect and disease resistance: Good resistance to scab, fire blight and codling moth, as determined from comparison with other varieties grown under comparable conditions at Geneva, New York.

I claim:

A new and distinct variety of crab apple tree, substantially as herein shown and described, characterized particularly as to novelty by the unique combination of attractive pendulous flowers and highly colored fruit, with attendant ornamental utility, an early bearing habit, a heavy and regular bearing habit, a relatively late ripening habit, suitability of the fruit for making excellent jelly, and good resistance to disease and insects, as well as to injury resulting from use of common spraying materials.

No references cited.